United States Patent
Yang

(10) Patent No.: US 10,646,440 B2
(45) Date of Patent: May 12, 2020

(54) SANGUISORBIGENIN POLYMER MICELLE AND PREPARATIVE METHODS THEREOF

(71) Applicant: SICHUAN INLU WEITE PHARMACEUTICAL TECHNOLOGY CO., LTD., Chengdu, Sichuan (CN)

(72) Inventor: Shilin Yang, Beijing (CN)

(73) Assignee: SICHUAN INLU WEITE PHARMACEUTICAL TECHNOLOGY CO., LTD., Chengdu, Sichuan (CN)

( * ) Notice: Subject to any disclaimer, the term of this patent is extended or adjusted under 35 U.S.C. 154(b) by 35 days.

(21) Appl. No.: 16/095,140

(22) PCT Filed: Nov. 7, 2016

(86) PCT No.: PCT/CN2016/104875
§ 371 (c)(1),
(2) Date: Oct. 19, 2018

(87) PCT Pub. No.: WO2017/181653
PCT Pub. Date: Oct. 26, 2017

(65) Prior Publication Data
US 2019/0142749 A1 May 16, 2019

(30) Foreign Application Priority Data
Apr. 21, 2016 (CN) .......................... 2016 1 0256965

(51) Int. Cl.
| A61K 9/107 | (2006.01) |
|---|---|
| A61K 9/00 | (2006.01) |
| A61K 31/19 | (2006.01) |
| A61K 47/34 | (2017.01) |
| A61K 9/19 | (2006.01) |
| A61K 31/56 | (2006.01) |
| A61P 7/06 | (2006.01) |

(52) U.S. Cl.
CPC .......... *A61K 9/1075* (2013.01); *A61K 9/0019* (2013.01); *A61K 9/107* (2013.01); *A61K 9/19* (2013.01); *A61K 31/19* (2013.01); *A61K 31/56* (2013.01); *A61K 47/34* (2013.01); *A61P 7/06* (2018.01)

(58) Field of Classification Search
CPC .... A61K 9/1075; A61K 9/0019; A61K 31/19; A61K 9/107; A61K 47/34; A61K 9/19; A61K 31/56; A61P 7/06
See application file for complete search history.

(56) References Cited

FOREIGN PATENT DOCUMENTS

| CN | 101119740 B | 2/2012 |
|---|---|---|
| CN | 104510716 A | 4/2015 |
| CN | 104856949 A | 8/2015 |

OTHER PUBLICATIONS

Lin, Hingying et al. "Block Copolymer Micelles as Delivery System for Poorly Soluble Antineoplastic Carrier" Chinese Traditional and Herbal Drugs, vol. 37, No. 04, Apr. 30, 2006, ISSN: 0253-2670, pp. 481-485, Considered to the extent of the English Abstract.
Zhu, Yuxuan et al. "Preparation of Polymer Drug-Loaded Micelles of Active Metabolites NG701 of Saponin Rb1 and their Invitro Cytotoxicity Evaluation" China Pharmacy, vol. 22, No. 17, May 31, 2011, ISSN: 1001-0408, pp. 1576-1579, Considered to the extent of the English Abstract.

*Primary Examiner* — Trevor Love
(74) *Attorney, Agent, or Firm* — Novick, Kim & Lee, PLLC; Allen Xue

(57) ABSTRACT

The present invention discloses a sanguisorbigenin polymer micelle, and it is prepared by following raw/auxiliary materials at predetermined weight ratio: 30 parts of sanguisorbigenin and 100-5000 parts of mPEG-PLA-Phe(Boc). Quality evaluation test indicates that only using mPEG-PLA-Phe(Boc) according to the present invention as carrier materials, the quality of sanguisorbigenin polymer micelle prepared is the best, and using other materials can lead to the lowered preparation quality. In pharmacodynamic experiment, compared with the model group, the sanguisorbigenin micelle of the present invention can significantly increase the amounts of WBC, RBC, PLT, NEUT, and HGB in peripheral blood, and the efficacy is obviously better than the original drug of sanguisorbigenin, indicating the sanguisorbigenin polymer micelle has a better treatment and/or prevention effects on bone marrow suppression, and can improve the bioavailability of insoluble drug of sanguisorbigenin.

10 Claims, No Drawings

SANGUISORBIGENIN POLYMER MICELLE AND PREPARATIVE METHODS THEREOF

TECHNICAL FIELD

The present invention relates to a sanguisorbigenin polymer micelle and preparative methods thereof, belonging to pharmaceutical field.

BACKGROUND ART

Bone marrow suppression is a common hematopoietic system disease seen in clinical practice, and many factors such as radiation damage caused by radiation therapy and/or chemotherapy of neoplastic diseases in various systems as well as ionizing radiation, viral hepatitis, parvovirus infection or drugs and the like can result in bone marrow suppression. Bone marrow suppression is mainly represented by injuries of bone marrow microenvironment, hematopoietic stem cells, hematopoietic cell growth factors, etc, together with inhibition of cells in one system, two systems and three systems of granulocytic system, erythrocytic system, and megakaryocytic system; amongst, agranulocytosis can cause severe infections, obvious reduction of erythrocytes can cause severe anemia, and obvious decrease of platelets can cause hemorrhage and even lead to death. Because marrow suppression seriously threatens lives and health of patients, especially producing adverse effects on neoplastic patients receiving chemoradiation, currently, many research groups are engaged in searching for potent drugs to prevent and curebone marrow suppression.

Sanguisorbigenin, a chemical name: 3β,19β-dihydroxyurs-12-en-28-oic acid, and its structure is shown as formula III:

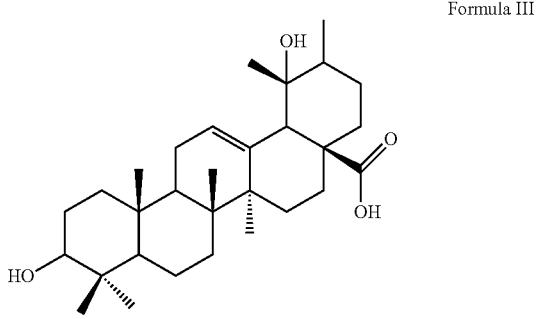

Formula III

Sanguisorbigenin is an active constituent extracted from roots of *Sanguisorba officinalis* L. or *S. officinalis* L. var. *longifolia* (Bertol.) Yu et Li, plants of *Sanguisorba* genus (Rosaceae). CN101119740A has disclosed the use of ziyuglycoside II in preparation of drugs elevating erythrocytes and hemoglobin. However, solubility of sanguisorbigenin in water is low, and gastrointestinal absorption rate after oral administration is low, that lead to low bioavailability of this drug taken orally and limit the application in clinical.

Polymer micelle, as a pharmaceutically acceptable carrier, can increase dissolution of insoluble drugs, and has characteristics of stable structure, good tissue permeability, long in vivo retention time, and making drugs effectively reach target point, etc, thus it is an excellent carrier for insoluble drugs. At present, a great variety of carrier materials are used for preparation of polymer micelles, and amphiphilic block copolymers are often utilized. Hydrophilic segment can be selected from polyethylene glycol, polyoxyethylene, povidone, chitosan, etc., while hydrophobic segment mainly includes polypropylene, polystyrene, polyamino acid, polylactic acid, spermine or short chain phosphatides, etc.

However, it is very difficult that drugs and polymer carrier materials are combined to prepare micelles with high drug-loading contents, small particle diameters or fitness for injection, and the quality of preparation depends largely on the chemical structures and physical properties of specific drugs. It is unpredictable whether professionals can choose and obtain suitable carrier materials that can combine with a specific drug to prepare micelles with better quality. Since little is known about the interaction of drug-carrier material, also, choosing suitable carrier materials is hard and time-consuming. According to the main pharmacological properties of the selection of the appropriate polymer material, so preparing micelles and obtaining preparations with quality meeting requirements, and allowing that drugs can be effectively released and produce effect in organism, is one of major problems for designing polymer micelles.

Consequently, there is an urgent need for developing a sanguisorbigenin polymer micelle with better preparation quality and definite efficacy, that can be used for treatment and/or prevention of bone marrow suppression.

CONTENT OF THE INVENTION

An object of the present invention is intended to provide a sanguisorbigenin polymer micelle and preparative methods thereof.

The present invention provides a polymer micelle, and it is prepared by following raw/auxiliary materials at predetermined weight ratio: 30 parts of sanguisorbigenin and 100-5000 parts of mPEG-PLA-Phe(Boc).

Further, it is prepared by following raw/auxiliary materials at predetermined weight ratio: 30 parts of sanguisorbigenin and 450-3600 parts of mPEG-PLA-Phe(Boc).

Preferably, it is prepared by following raw/auxiliary materials at predetermined weight ratio: 30 parts of sanguisorbigenin and 900-3600 parts of mPEG-PLA-Phe(Boc).

Further preferably, it is prepared by following raw/auxiliary materials at predetermined weight ratio: 30 parts of sanguisorbigenin and 1800 parts of mPEG-PLA-Phe(Boc).

Wherein, the polymer micelle further contains 0-5000 parts of sugar, in which said sugar is selected from glucose, sucrose, trehalose, fructose, mannitol or lactose.

Wherein, the number average molecular weight of mPEG in mPEG-PLA-Phe(Boc) is 2000-5000, and the number average molecular weight of PLA in mPEG-PLA-Phe(Boc) is 3000-5000.

Further, the number average molecular weight of mPEG in mPEG-PLA-Phe(Boc) is 2000, and the number average molecular weight of PLA in mPEG-PLA-Phe(Boc) is 4000.

The present invention provides a method for preparing the polymer micelle, including the following steps: various weight ratios of sanguisorbigenin and mPEG-PLA-Phe(Boc) are dissolved in 12-125 times volume of ethanol, and then ethanol is evaporated to obtain the polymer micelle.

Further, the preparative method further includes following steps: 0-5000 parts of sugar, together with the polymer micelle, is dissolved in water at the same time, allowing the concentration of sanguisorbigenin to be 0.01 mg/mL-20 mg/mL, and then filtered with 0.22 μm micropore film, followed by freeze-drying, to obtain lyophilized powder of polymer micelle.

The present invention provides the uses of polymer micelle in preparation of drugs for treatment and/or prophylaxis of bone marrow suppression.

Further, drugs are those which used for treatment and/or prevention of bone marrow suppression induced by chemical substances.

More further, drugs are those which can increase one or more of white blood cells (WBC), neutrophilic granulocytes (NEUT), red blood cells (RBC), platelets (PLT) or hemoglobin (HGB) in peripheral blood.

The present invention provides a method for treatment and/or prophylaxis of bone marrow suppression, and it is using the said polymerizationmicelles.

The present invention provides a sanguisorbigenin polymer micelle and a preparative method thereof. Quality evaluation experiments indicates that the prepared sanguisorbigenin polymer micelle has the best quality when using mPEG-PLA-Phe(Boc) as the carrier materials of the invention, and using additional materials can lead to the lowered preparation quality. In pharmacodynamic experiment, compared with the model group, the sanguisorbigenin micelle of the present invention can significantly increase the amounts of WBC, RBC, PLT, NEUT, and HGB in peripheral blood, and the efficacy is obviously better than the original drug sanguisorbigenin. It is proved that the sanguisorbigenin polymer micelle of the present invention has a better treatment and/or prevention effects on bone marrow suppression, and can improve the bioavailability of insoluble drug sanguisorbigenin.

Obviously, based on above contents of the present invention, without departing from above basic technical spirit of the present invention, various additional modifications, substitutions and alterations can also be made by common technical knowledge and commonly-used means in the field.

Hereinafter, the above content of present invention can further be illustrated in detail, combined with specific examples. But it should not be understood that above subject scope of the present invention is only limited to the following examples. The techniques, realizable based on above contents, should all be within the scope of the present invention.

EXAMPLES

Raw materials and equipments used in specific examples of the present invention are all known and can be obtained by buying commercially available products.

Example 1 Preparation of Polymer Micelles According to the Present Invention 30 mg sanguisorbigenin and 1500 mg mPEG1000-PLA1000-Phe(Boc) were dissolved in 15 ml ethanol, and the solvent was removed by rotary evaporation at 55° C. 50 ml injectable sugar water (containing 5 g glucose) was added to dissolve drug membrane, and the obtained micelle solution was filtered by 0.22 μm sterile film and freeze-dried, to get lyophilized powder of sanguisorbigenin micelle.

Example 2 Preparation of Polymer Micelles According to the Present Invention 30 mg sanguisorbigenin and 900 mg mPEG1000-PLA1000-Phe(Boc) were dissolved in 15 ml ethanol, and the solvent was removed by rotary evaporation at 55° C. 50 ml injectable sugar water (containing 5 g glucose) was added to dissolve drug membrane, and the obtained micelle solution was filtered by 0.22 μm sterile film and freeze-dried, to get lyophilized powder of sanguisorbigenin micelle.

Reconstitution of above lyophilized powder of sanguisorbigenin micelle in solvents was good, and the change of size distribution before and after reconstitution was small. The content of principal drug was 0.4 mg/mL, with an entrapment rate of >99%, a particle size of <100 nm, and PDI of <0.3.

Example 3 Preparation of Polymer Micelles According to the Present Invention 30 mg sanguisorbigenin and 1200 mg mPEG1000-PLA1000-Phe(Boc) were dissolved in 50 ml ethanol, and the solvent was removed by rotary evaporation at 55° C.

50 ml injectable sugar water (containing 5 g glucose) was added to dissolve drug membrane, and the obtained micelle solution was filtered by 0.22 μm sterile film and freeze-dried, to get lyophilized powder of sanguisorbigenin micelle.

Example 4 Preparation of Polymer Micelles According to the Present Invention 30 mg sanguisorbigenin and 1800 mg mPEG1000-PLA1000-Phe(Boc) were dissolved in 50 ml ethanol, and the solvent was removed by rotary evaporation at 55° C.

50 ml injectable sugar water (containing 5 g glucose) was added to dissolve drug membrane, and the obtained micelle solution was filtered by 0.22 μm sterile film and freeze-dried, to get lyophilized powder of sanguisorbigenin micelle.

Hereinafter, the beneficial effects of the present invention were demonstrated by following examples.

Assaying:

Apparatus: High performance liquid chromatograph Waters e2695

Chromatographic condition: chromatographic column: octadecylselyl bonded silica gel (4.6×250 mm, 5 μm)

Detection wavelength: 203 nm

Mobile phase: methanol:0.1% formic acid=80:20

Flow rate: 1 mL/min

Column temperature: 25° C.

Sample size: 204,

Sample preparation: The solution of sanguisorbigenin micelle was diluted suitable multiples with MeOH, and injected to high performance liquid chromatograph to measure the particle size and distribution.

Determination of particle size and distribution:

Apparatus: Malvern ZS90

Sample preparation: The solution of sanguisorbigenin micelle was diluted suitable multiples with ultrapure water, and injected to particle size analyzer to measure the particle size and distribution.

Example 1 Quality Evaluation of Polymer Micelles Prepared with Different Carrier Materials At the early stage of the present study, according to properties of sanguisorbigenin, various amphiphilic block copolymers constituted by hydrophilic materials and hydrophobic materials were investigated, and five materials providing better quality of polymer micelles were listed in the following.

1. mPEG-PLA-Phe(Boc): tert-butoxyphenylalanine-terminated methoxypolyethylene glycol-polylactic acid block copolymer, its hydrophilic chain is mPEG with a number average molecular weight of 1000-5000, and its lipophilic chain is PLA with a number average molecular weight of 1000-5000, and its structure is shown as formula I:

Formula I

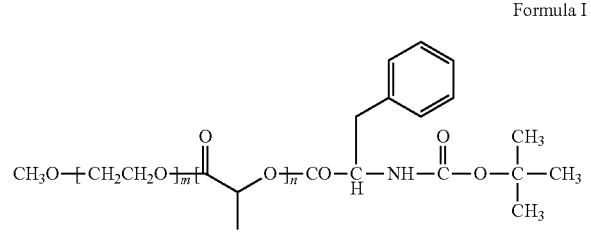

For the synthetic method of high molecular polymer, seeing references: [1] Chen xue-dong, Yang shi-lin, Feng yu-lin, Liu ke, et al, Preparation and characterization of arctigenin mPEG-PDLLA polymer micelles [J]. Medicine, 2015, 18(8): 153; [2] Chen xue-dong, Preparation and evaluation of a new carrier docetaxel mPEG-PDLLA-Phe (Boc) micelles, Master degree thesis of Jiangxi University of Traditional Chinese Medicine, 2016.6.

2. mPEG-PLA: methoxypolyethylene glycol-polylactic acid block copolymer, its hydrophilic chain is mPEG with a number average molecular weight of 1000-5000, and its lipophilic chain is PLA with a number average molecular weight of 1000-5000, and its structure is shown as formula II:

Formula II

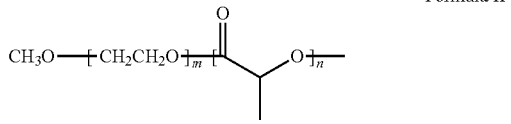

The synthetic method of high molecular polymeris showing in the above references.

3. Poloxamer F68, i.e. Poloxamer, is a polyoxyethylene polyoxypropylene block copolymer.
4. Solutol HS15 is a polyethylene glycol-12-hydroxystearate.
5. Polyoxyethylene castor oil EL35.

Poloxamer F68, Solutol HS15, and polyoxyethylene castor oil EL35 were all purchased from BASF company, Germany.

Experimental Method 1. 30 mg Sanguisorbigenin and 900 mg different high polymer materials which weremPEG2000-PLA4000-Phe(Boc), mPEG2000-PLA4000, Poloxamer F68, Solutol HS15, and polyoxyethylene castor oil EL35 were dissolved in 15 ml EtOH, respectively. After removal of solvents by rotary evaporation at 55° C., 50 ml water for injection was added to dissolve drug membrane. After the obtained micelle solution was filtered by 0.22 μm sterile film, the content of sanguisorbigenin in micelles and its particle size distribution were measured, and results were shown in Table 1.

TABLE 1

Quality evaluation of polymer micelles prepared with different carrier materials

| Carrier materials | Content of drug (mg/mL) | Mean diameter (nm) | PDI |
|---|---|---|---|
| mPEG-PLA-Phe(Boc) | 0.588 | 69 | 0.19 |
| mPEG-PLA | 0.215 | 179 | 0.28 |
| Poloxamer F68 | 0.091 | 57 | 0.11 |
| Solutol HS15 | 0.167 | 48 | 0.21 |
| polyoxyethylene castor oil EL35 | 0.154 | 33 | 0.13 |

Experimental results: the content of sanguisorbigenin was the highest (up to 0.588 mg/mL) in polymer micelles prepared by carrier materials mPEG-PLA-Phe(Boc) according to the present invention, the mean diameter was smaller (69 nm), and the dispersion index (PDI) was only 0.19, indicating the particle size of obtained micelles was very uniform. Two additional materials which were mPEG-PLA and Poloxamer F68 can obviously reduce the content of drug or the uniformity of particle diameter, moreover, the mean diameter of micelles by using mPEG-PLA was bigger and unsuitable for injection. Using Solutol HS15 and polyoxyethylene castor oil EL35 also had a problem that the content of drug decreased.

Above experimental results indicated: when mPEG-PLA-Phe(Boc) was used as the only carrier materials of the present invention, the quality of sanguisorbigenin polymer micelles prepared was the best, the preparation quality decreased when using other materials.

2. 30 mg Sanguisorbigenin and 900 mg mPEG-PLA-Phe(Boc) with different number average molecular weight were dissolved in 15 ml EtOH, respectively. After removal of solvents by rotary evaporation at 55° C., 50 ml water for injection was added to dissolve drug membrane.

After the obtained micelle solution was filtered by 0.22 μm sterile film, the content of sanguisorbigenin in micelles and its particle size distribution were measured, and results were shown in Table 2.

TABLE 2

Quality evaluation of polymer micelles prepared by using mPEG-PLA-Phe(Boc) with different molecular weight

| Number average molecular weight of carrier materials | Content of drug (mg/mL) | Mean diameter (nm) | PDI |
|---|---|---|---|
| mPEG1000-PLA1000-Phe(Boc) | 0.085 | 211 | 0.29 |
| mPEG2000-PLA1000-Phe(Boc) | 0.11 | 185 | 0.23 |
| mPEG5000-PLA3000-Phe(Boc) | 0.591 | 220 | 0.18 |
| mPEG2000-PLA4000-Phe(Boc) | 0.588 | 69 | 0.19 |
| mPEG2000-PLA5000-Phe(Boc) | 0.581 | 310 | 0.27 |

Experimental results: when mPEG-PLA-Phe(Boc) was used with a number average molecular weight in the range of the present invention, the sanguisorbigenin polymer micelles can be prepared; amongst, the content of sanguisorbigenin was the highest (up to 0.588 mg/mL) in polymer micelles prepared by carrier materials mPEG-PLA-Phe(Boc), the mean diameter was smaller (69 nm), and the dispersion index (PDI) was only 0.19, indicating the quality of obtained micelles was the best.

Example 2 Quality Evaluation of Polymer Micelles which were Prepared with the Different Carrier Materials Amounts Sanguisorbigenin and MPEG2000-PLA4000-Phe(Boc) were weighed and taken out at a mass ratio of 1:10-1:120 (the weight of sanguisorbigenin was fixed to 30 mg, and the weight of MPEG-PLA-Phe(Boc) can be changed as the ratio), and were dissolved in 50 ml EtOH, respectively. After removed solvents by rotary evaporation at 55° C., 50 ml water for injection was added to dissolve drug membrane. After the obtained micelle solution was filtered by 0.22 μm sterile film, the content of sanguisorbigenin in micelles and its particle size distribution were measured, and results were shown in Table 3.

TABLE 3

Quality evaluation of polymer micelles which were prepared with the different carrier materials amounts

| (mass ratio) sanguisorbigenin:mPEG-PLA-Phe(Boc) | Content of drug (mg/mL) | Mean diameter (nm) | PDI |
|---|---|---|---|
| 1:10  | 0.109 | 139 | 0.24 |
| 1:15  | 0.279 | 112 | 0.27 |
| 1:30  | 0.588 | 69  | 0.19 |
| 1:60  | 0.593 | 71  | 0.18 |
| 1:120 | 0.602 | 78  | 0.16 |

Experimental results: when the usage amount of carrier material MPEG-PLA-Phe(Boc) was 15-20 times than sanguisorbigenin, the quality of obtained polymer micelles was better: the least content of drug was 0.2 mg/mL, the mean diameter was below 112 nm, and PDI was all below 0.3. The preparation quality could be further optimized when the usage amount of MPEG-PLA-Phe(Boc) was in the range of 30-120 times than sanguisorbigenin. It was shown by the higher content of drug which can reach 0.5 mg/mL or more, the mean diameter was below 80 nm, and PDI of less than 0.2. Comprehensive comparison, when the mass ratio of sanguishorbigenin and mPEG-PLA-Phe(Boc) was 1:60, the quality of micelles was the best: the content of drug was higher, the mean diameter was smaller, and the size distribution was more uniform.

Example 3 Pharmacodynamic Experiment of Sanguisorbigenin Polymer Micelles of the Present Invention 1. Experimental Materials, Reagents, Apparatus Test drugs were sanguisorbigenin micelles and sanguisorbigenin powder.

Tool drug was cyclophosphamide.

Laboratory animals were KM-mice: 18.5-22.5 g.

Laboratory apparatus: Automatic hematology analyzer; BS-600L electronic balance: specification: 600 g/0.1 g, Shanghai Yousheng Weighing Apparatus Co. Ltd.

2. Statistical Method

Statistical analysis was performed using SPSS 17.0 software. Data were expressed as mean±standard error ($\bar{x}±s$) and one-factor analysis of variance was used among groups. For homogeneity of variance, data between groups were compared by LSD test, while for heterogeneity of variance, data between groups were compared by Tamhane's T2 test.

3. Experimental Method 3.1 Grouping of Laboratory Animals and Establishing Model After all laboratory animals were adaptively fed for one week, according to the body weight, animals were randomly divided as blank group, model group, sanguisorbigenin micelle sample groups 1-4 andsanguisorbigenin group. The sanguisorbigenin micelle sample groups 1-4 respectively used micelles prepared in examples 1-4, and the dose was 2.5 mg·kg$^{-1}$. The sanguisorbigenin group used powder of sanguisorbigenin raw materials which dissolved in 10% DMSO-normal saline, and the dose was 2.5 mg·kg$^{-1}$. On the first day of experiment, except for blank group, mice in other groups received cyclophosphamide normal saline solution at a dose of 120 mg·kg$^{-1}$ by peritoneal injection, and mice in blank group received the same volume of normal saline by peritoneal injection.

3.2 Administration

From the first day of experiment, each experimental group was given the corresponding drug as the predetermined dosage and administration mode, and mice in blank group and model group were given a same volume of normal saline by injection into the tail vein, for successive 6 days.

3.3 Sample Collection

On the seventh day of experiment, whole blood was collected from orbit of mice in each experimental group, and placed in 0.5 ml EP tubes containing EDTA anticoagulant agent for test.

3.4 Detection Index and Method

White blood cells (WBC), neutrophilic granulocytes (NEUT), red blood cells (RBC), platelets (PLT), and hemoglobin (HGB) in peripheral blood of mice in each experimental group were counted using automatic blood counting instrument.

4. Experimental Results

TABLE 4

Numbers of WBC, RBC. and PLT in peripheral blood of mice in each experimental group.

| Groups | Dosage (mg/kg) | WBC (×10$^9$) | RBC (×10$^{12}$) | PLT (×10$^9$) |
|---|---|---|---|---|
| Blank group     | —   | 6.25 ± 0.16$^{Δ*}$ | 5.87 ± 0.36$^{Δ*}$ | 468.16 ± 9.36$^{Δ*}$ |
| Model group     | —   | 2.48 ± 0.18        | 3.01 ± 0.36        | 226.54 ± 13.65 |
| Micelle sample① | 2.5 | 6.13 ± 0.19$^{Δ*}$ | 5.19 ± 0.16$^{Δ*}$ | 426.94 ± 14.56$^{Δ*}$ |
| Micelle sample② | 2.5 | 5.84 ± 0.21$^{Δ*}$ | 5.06 ± 0.23$^{Δ*}$ | 433.58 ± 12.35$^{Δ*}$ |
| Micelle sample③ | 2.5 | 5.97 ± 0.12$^{Δ*}$ | 5.15 ± 0.87$^{Δ*}$ | 429.83 ± 11.35$^{Δ*}$ |

TABLE 4-continued

Numbers of WBC, RBC. and PLT in peripheral blood of mice in each experimental group.

| Groups | Dosage (mg/kg) | WBC ($\times 10^9$) | RBC ($\times 10^{12}$) | PLT ($\times 10^9$) |
|---|---|---|---|---|
| Micelle sample④ | 2.5 | 6.11 ± 0.47$^{\Delta*}$ | 5.09 ± 0.81$^{\Delta*}$ | 435.02 ± 15.65$^{\Delta*}$ |
| Sanguisorbigenin group | 2.5 | 2.79 ± 0.26 | 3.15 ± 0.19 | 231.16 ± 15.27 |

Note:
compared with model group,
*P < 0.05,
**P < 0.01;
Note:
compared with sanguisorbigenin group,
$^{\Delta}$p < 0.05,
$^{\Delta\Delta}$p < 0.01.

Experimental results: compared with model group, numbers of WBC, RBC, and PLT in peripheral blood of mice in groups 1-4 of sanguisorbigenin micelle sample according to the present invention was significantly increased (P<0.05), while sanguisorbigenin group did not show significant difference; compared with sanguisorbigenin group, numbers of WBC, RBC, and PLT in peripheral blood of mice in groups 1-4 of sanguisorbigenin micelle sample according to the present invention was significantly increased (P<0.05).

TABLE 5

Numbers of NEUT and HGB in peripheral blood of mice in each experimental group.

| Groups | Dosage (mg/kg) | NEUT ($\times 10^9$) | HGB (g/L) |
|---|---|---|---|
| Blank group | — | 6.76 ± 0.58$^{\Delta*}$ | 97.45 ± 12.65$^{\Delta*}$ |
| Model group | — | 2.39 ± 0.37$^{\Delta}$ | 42.48 ± 8.89$^{\Delta}$ |
| Micelle sample① | 2.5 | 5.99 ± 0.47$^{\Delta*}$ | 88.53 ± 10.45$^{\Delta*}$ |
| Micelle sample② | 2.5 | 6.02 ± 0.85$^{\Delta*}$ | 92.61 ± 9.34$^{\Delta*}$ |
| Micelle sample③ | 2.5 | 5.78 ± 0.35$^{\Delta*}$ | 89.97 ± 12.67$^{\Delta*}$ |
| Micelle sample④ | 2.5 | 5.85 ± 0.92$^{\Delta*}$ | 89.45 ± 9.554$^{\Delta*}$ |
| Sanguisorbigenin group | 2.5 | 2.56 ± 0.13 | 45.47 ± 8.39 |

Note:
compared with model group,
*P < 0.05,
**P < 0.01;
Note:
compared with sanguisorbigenin group,
$^{\Delta}$p < 0.05,
$^{\Delta\Delta}$p < 0.01.

Experimental results: compared with model group, numbers of NEUT and HGB in peripheral blood of mice in groups 1-4 of sanguisorbigenin micelle sample according to the present invention was significantly increased (P<0.05), while sanguisorbigenin group did not show significant difference; compared with sanguisorbigenin group, numbers of NEUT and HGB in peripheral blood of mice in groups 1-4 of sanguisorbigenin micelle sample according to the present invention was significantly increased (P<0.05).

Above experimental results indicated: the sanguisorbigenin polymer micelle of the present invention has a better treatment and/or prevention effects on bone marrow suppression, and the efficacy was obviously better than direct administration of sanguisorbigenin raw materials.

The invention claimed is:

1. A polymer micelle, comprising 30 weight parts of sanguisorbigenin and 100-5000 weight parts of mPEG-PLA-Phe(Boc).

2. The polymer micelle according to claim 1, comprising 30 weight parts of sanguisorbigenin and 450-3600 weight parts of mPEG-PLA-Phe(Boc).

3. The polymer micelle according to claim 2, comprising 30 weight parts of sanguisorbigenin and 900-3600 weight parts of mPEG-PLA-Phe(Boc).

4. The polymer micelle according to claim 3, comprising 30 weight parts of sanguisorbigenin and 1800 weight parts of mPEG-PLA-Phe(Boc).

5. The polymer micelle according to claim 4, further comprising less than 5000 weight parts of sugar, wherein the sugar is selected from the group consisting of glucose, sucrose, trehalose, fructose, mannitol, lactose, and mixtures thereof.

6. The polymer micelle according to claim 1, wherein a number average molecular weight of mPEG in mPEG-PLA-Phe(Boc) is 2000-5000, and a number average molecular weight of PLA in mPEG-PLA-Phe(Boc) is 3000-5000.

7. The polymer micelle according to claim 6, wherein the number average molecular weight of mPEG in mPEG-PLA-Phe(Boc) is 2000, and the number average molecular weight of PLA in mPEG-PLA-Phe(Boc) is 4000.

8. A method for preparing the polymer micelle according to claim 1, comprising: dissolving sanguisorbigenin and mPEG-PLA-Phe(Boc) in ethanol; and evaporating the ethanol to obtain the polymer micelle.

9. The method according to claim 8, further comprising: dissolving sugar and the polymer micelle in water to obtain a solution having a concentration of sanguisorbigenin of 0.01 mg/mL-20 mg/mL, then filtering the solution; then freeze-drying, to obtain a lyophilized powder of polymer micelle.

10. A method for treatment and/or prophylaxis of bone marrow suppression, comprising administering a pharmaceutically suitable amount of the polymer micelle of claim 1 to a subject in need thereof.

* * * * *